(12) United States Patent
Blackbeard et al.

(10) Patent No.: US 9,610,144 B2
(45) Date of Patent: Apr. 4, 2017

(54) DENTAL IMPLANT ASSEMBLY INCLUDING A LOW FRICTION WASHER

(75) Inventors: Graham Alan Blackbeard, Centurion (ZA); Heather Madeleine Coombes, Pretoria (ZA); Leith Cumming, Centurion (ZA)

(73) Assignee: SOUTHERN IMPLANTS (PTY) LTD, Centurion (ZA)

( * ) Notice: Subject to any disclaimer, the term of this patent is extended or adjusted under 35 U.S.C. 154(b) by 0 days.

(21) Appl. No.: 13/263,604

(22) PCT Filed: Apr. 7, 2010

(86) PCT No.: PCT/IB2010/051501
§ 371 (c)(1),
(2), (4) Date: Nov. 22, 2011

(87) PCT Pub. No.: WO2010/116330
PCT Pub. Date: Oct. 14, 2010

(65) Prior Publication Data
US 2012/0100503 A1    Apr. 26, 2012

(30) Foreign Application Priority Data
Apr. 8, 2009   (ZA) ................. 2009/02456

(51) Int. Cl.
*A61C 8/00* (2006.01)
(52) U.S. Cl.
CPC ............ *A61C 8/005* (2013.01); *A61C 8/0068* (2013.01)
(58) Field of Classification Search
CPC ....... A61C 8/00; A61C 8/0012; A61C 8/0018; A61C 8/0022; A61C 8/0048; A61C 8/005; A61C 8/0054; A61C 8/0057; A61C 8/0059; A61C 8/006; A61C 8/0065; A61C 8/0066; A61C 8/0068; A61C 8/0069; A61C 8/0075; A61C 8/0078; A61C 8/0086
USPC ...................................... 433/172–176, 201.1
See application file for complete search history.

(56) References Cited

U.S. PATENT DOCUMENTS

| 4,756,689 | A | 7/1988 | Lundgren et al. | |
| 5,125,839 | A * | 6/1992 | Ingber et al. | 433/169 |
| 6,447,295 | B1 | 9/2002 | Kumar et al. | |
| 7,300,282 | B2 * | 11/2007 | Sapian | 433/173 |
| 2006/0078844 | A1 | 4/2006 | Goldman et al. | |
| 2007/0072148 | A1 * | 3/2007 | Memmolo et al. | 433/141 |
| 2009/0075236 | A1 * | 3/2009 | Towse et al. | 433/174 |

* cited by examiner

*Primary Examiner* — Ralph Lewis
(74) *Attorney, Agent, or Firm* — Nixon Peabody LLP

(57) ABSTRACT

The invention concerns a dental implant assembly including an implant component (10) which is engaged in use with a bone structure and which has an internally threaded socket (14). The assembly also includes a dental component (20), typically an abutment, crown or prosthetic tooth, which seats on the implant component and which has a passage (24) through its base (22). The dental component is clamped to the implant component by a prosthetic retaining screw (28) having a head (32) and a shank (30) which passes through the passage and is screwed into the socket of the implant component. The invention is characterized in that a separate washer (36) including a low friction polymeric material is located rotatably on the shank of the screw adjacent the screw head in order to reduce friction between the head of the screw and the base of the dental component when the screw is tightened up.

25 Claims, 1 Drawing Sheet

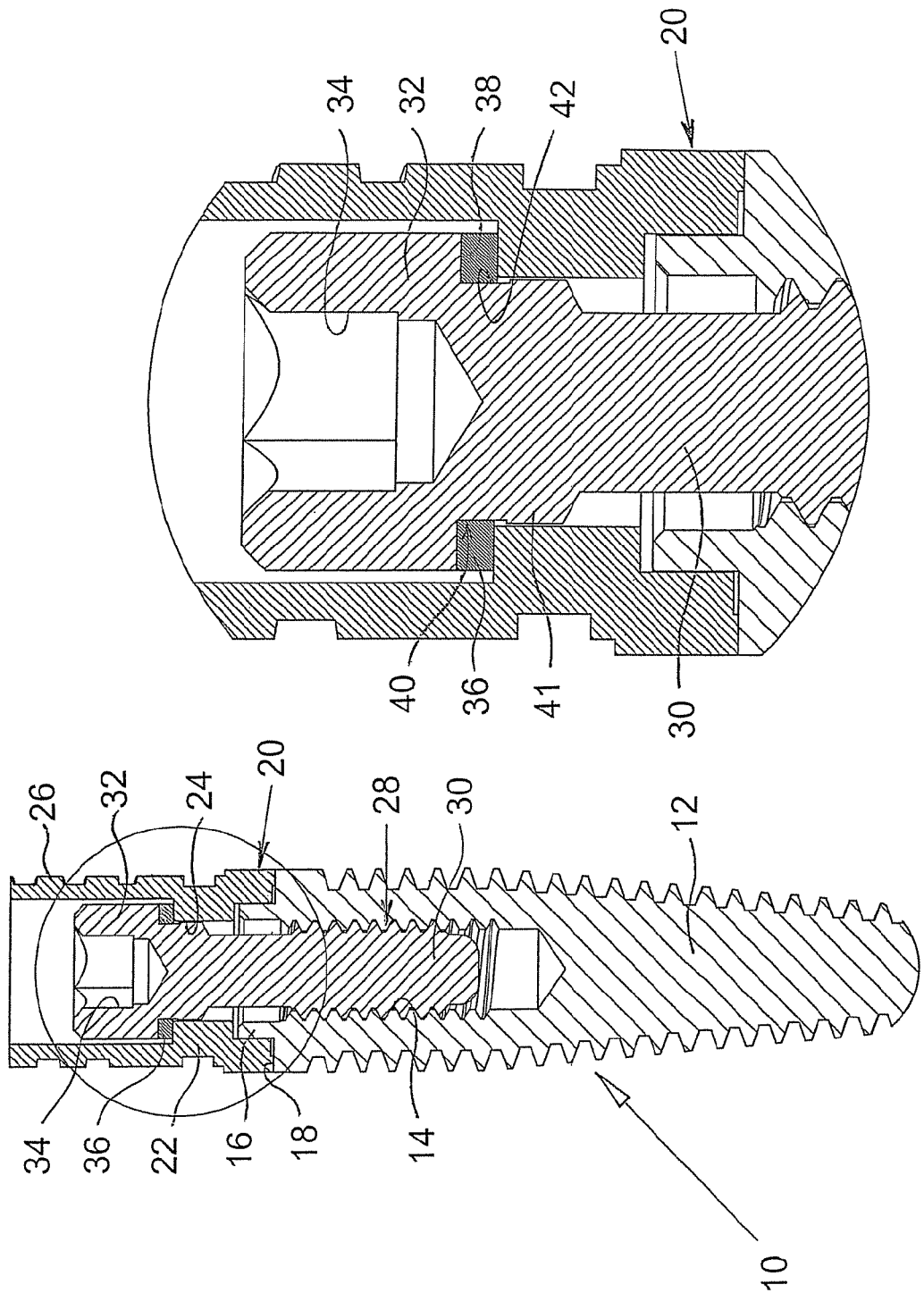

DENTAL IMPLANT ASSEMBLY INCLUDING A LOW FRICTION WASHER

BACKGROUND TO THE INVENTION

THIS invention relates to a dental implant assembly and sub-assembly.

A dental implant is an artificial tooth root replacement and is used in prosthetic dentistry to support restorations that resemble a tooth or group of teeth. Known dental implant assemblies of the osseointegrated type have three components. One of these is the implant or fixture component which takes the place of the natural tooth root and which is anchored in the jaw bone of the patient. This component is normally made of metal, typically titanium, or a ceramic, typically zirconium oxide, and has an external thread: which is engaged in a hole drilled, reamed or otherwise formed in the jaw bone. The component also has an internally threaded socket to receive a prosthetic screw as described below.

Another component of the dental implant is a dental component, typically a crown or abutment which seats on the apical or outer end of the implant component. The crown or abutment has a passage through it which aligns with the socket in the implant component. In use, it is fixed or clamped to the implant component by a component in the form of a retaining screw which passes through the passage in the abutment and is screwed into the socket.

It is desirable for the preload force applied by the screw, which serves to clamp together the fixture and crown or abutment components, to be as high as possible. It is recognised that the greater the tension in the screw, the greater the "preload" force with which the crown or abutment is clamped to the implant component. If there is an insufficient preload force the prosthetic screw may come loose, or the connection may not remain closed or may suffer from instability when functional loading, for example during mastication, is applied thereto.

Threaded advance of the screw into the socket is at least partially resisted by friction between rotating surfaces of the screw and the stationary surfaces against which the screw moves. In the prior art, it has been recognised that by reducing the frictional resistance, the preload on the screw can be increased for a given applied torque. Examples of attempts to reduce frictional resistance are described in the following documents:

U.S. Pat. No. 5,711,669—this document describes an assembly in which the screw has a relatively soft, malleable coating of gold or silver.

U.S. Pat. Nos. 5,879,161 and 6,287,116—these documents describe assemblies in which the screw is gold-plated for reduced friction.

U.S. Pat. No. 6,447,295—this document describes an assembly in which the screw is coated with a hard carbon coating or film to reduce friction. The hard carbon coating may be in the form of diamond-like carbon, amorphous diamond, crystalline diamond or a combination of such materials.

U.S. Pat. No. 7,300,283—this document describes a retaining screw fitted with a rotationally fixed spring washer made of gold to reduce friction between the head of the screw and the component against which it acts, typically the abutment.

It will be seen that in the majority of these prior art disclosures, attempts have been made to reduce friction between the rotating screw and the stationary surfaces against which it moves during the screw torqueing operation using gold or other relatively low friction metals. However experimentation by the present applicant has shown that the use of gold in or on the retaining screw or in an intervening washer provides only a modest increase in the preload force which can be obtained.

SUMMARY OF THE INVENTION

According to one aspect of the present invention there is provided a dental implant assembly comprising an implant component engagable with a bone structure and having an internally threaded socket, a dental component which is seatable on the implant component and which has a passage through a base thereof, a prosthetic retaining screw having a head and a shank which passes through the passage and is screwed into the socket of the implant component, thereby to clamp the dental component to the implant component, characterised in that a separate washer including a low friction polymeric material is located rotatably on the shank of the screw adjacent the head thereof in order to reduce friction between the head of the screw and the base of the dental component when the screw is tightened up.

Preferably the washer is made of or includes PEEK (polyether ether ketone), and is held axially captive on the shank of the screw.

According to another aspect of the invention there is provided a dental sub-assembly comprising a prosthetic screw having a head and a threaded shank which is engagable in a threaded socket in an implant component in order to clamp a dental component through which the screw passes in use to the implant component, characterised in that a separate washer including a low friction polymeric material is located rotatably on the shank of the screw adjacent the head thereof in order to reduce friction between the head of the screw and the dental component when the screw is tightened up.

Other features of the dental implant assembly and sub-assembly of the invention are set forth in the appended claims.

BRIEF DESCRIPTION OF THE DRAWINGS

The invention will now be described in more detail, by way of example only, with reference to the accompanying drawings in which:

FIG. 1 shows a cross-sectional view of components of a dental implant assembly according to this invention; and FIG. 2 shows an enlarged view of the encircled area in FIG. 1.

DESCRIPTION OF PREFERRED EMBODIMENTS

FIG. 1 shows components of a dental implant assembly including an implant component 10 having an externally threaded shank 12 and an internally threaded socket 14. At its apical or outer end, the component 10 has a protruding, hexagonal section boss 16 bounded by a flat land 18. In use, a spanner or other suitable tool is engaged with the boss and is used to screw the implant component into a hole drilled, reamed or otherwise formed in a patient's jawbone (not shown). With passage of time, the shank 12 becomes osseointegrated with the patient's bone structure and is accordingly firmly anchored to the jawbone.

The numeral 20 indicates a dental component in the form of an abutment which has an inner end complemental in shape to the apical end of the implant component, enabling the abutment to seat on the implant component as shown.

The abutment includes a base 22 through which a passage 24 is formed. When the abutment is seated on the implant component, the passage 24 aligns axially with the socket 14. The abutment also has an upstanding, hollow portion 26 on which, in use, a crown (not shown) can be mounted.

The assembly of abutment and crown is connected to the implant component by means of a prosthetic screw 28 which has a threaded shank 30 and an enlarged head 32 in which a hexagonal section socket 34 is formed. In accordance with the invention, a washer 36 is located about the shank 30 of the screw adjacent the underside 38 of the head 32.

In this embodiment, the implant component 10 and abutment 20 are each made in one piece of a suitable biocompatible metal such as titanium or a suitable ceramic such as zirconium oxide.

The screw 28 is also made of one piece of a suitable biocompatible material. This may for example be titanium or stainless steel. The washer 36 is made of a low friction material, in this case a low friction polymer. The preferred polymer is PEEK (polyether ether ketone).

The washer is prefitted to the shank 30 of the screw 28 under factory conditions. This avoids the need to fit the washer, which is typically very small in diameter, onto the shank, which is also typically of very small diameter, during an implantation procedure. Preferably the arrangement is such that the washer is rotatable on the shank but its axial position on the shank is maintained on the shank, so that it is not able simply to fall off.

FIG. 2 shows a preferred arrangement in which the shank 30 of the screw is formed with an annular groove or recess 40 directly beneath the underside 38 of the head 32, between head and a radially enlarged region 41 of the shank.

The relaxed internal diameter of the washer 36 is less than the external diameter of the enlarged region 41, and possibly also less than the external diameter of the main part of the shank 30 of the screw. The polymeric material of which the washer has a degree of elastic or resilient stretchability. This enables the washer to be stretched radially to an appropriate extent, during assembly in the factory, to enable it pass over the shank of the screw, including the enlarged region 41, from the distal or inner end thereof, so as to be located in the groove. Once in the groove the washer reverts to its original, relaxed diameter with the result that the washer is held axially captive in the groove.

The internal diameter of the washer is equal to or slightly greater than the diameter of the base 42 of the groove 40, allowing the washer to rotate about the shank of the screw once in position in the groove.

FIG. 1 shows the screw 28 with its shank extending through the opening 24 in the base of the abutment, through the washer and threaded into the socket 14. Torque is applied to the screw by means of a suitable tool applied to the hexagonal socket 34.

In the absence of the washer 36, there would direct contact between the underside of the head 32 and the base 22 of the abutment 20. This interaction would create substantial frictional resistance as the screw is tightened up. Assuming that only a predetermined amount of torque is applied to the screw, the preload which the screw generates to clamp the abutment to the implant component is accordingly limited.

However with the washer 36 in place, there is no direct rotational contact between the underside of the head of the screw and the base of the abutment. Rotational contact is between the underside of the head of the screw and the washer and/or between the washer and the base of the abutment. Because the washer is made of a low friction material there is, overall, less frictional resistance to screw rotation. It is accordingly possible to achieve, with the same applied torque, a higher screw preload force, leading to a tighter and more secure connection between the abutment and the implant component than is possible in the absence of the washer. The higher preload or clamping force which is attained reduces the chances of separation of the abutment 20 from the implant component 10, and hence reduces of any unsightly gap opening up between these components.

It will be understood that although the washer reduces frictional resistance which would otherwise be generated by the interaction between the head of the screw and the base of the abutment, frictional resistance as a result of the interaction between the threads of the screw and socket may still be significant. The overall frictional resistance may be reduced further by making the entire screw out of low friction material such as a gold alloy, by coating or plating the entire screw with such a low friction material or by coating or plating only selected surfaces of the screw, for example the threads, with such material.

In one preferred arrangement, however, the screw is made at least primarily of stainless steel. This is preferred to other materials, such as titanium, for the reason that stainless steel has reduced elasticity which enables a higher preload or clamping force to be attained without axial stretching and possible deformation of the screw which could in turn lead to a loss of the initially applied preload. Where stainless steel is used for the screw, relevant surfaces thereof, for example the screw threads, may be plated or lined with low friction material such as gold or a gold alloy.

In other, non-illustrated embodiments of the invention, the groove 40 may be omitted. In this case the washer is held axially captive by virtue of its internal diameter being smaller than the remaining, distal part of the shank of the screw. As yet another alternative, it is possible for the internal diameter of the washer to matched to the external diameter of the shank 30 such that light frictional contact between the washer and shank is sufficient to hold the washer axially in place while not removing the ability of the of the washer to rotate on the shank.

In each case it is an advantage of the invention that the washer is held axially captive on the shank of the screw since this enables the sub-assembly of screw and washer to be made up under factory conditions and supplied as a pre-assembled unit.

While the washer could also be made of other low friction polymeric materials, PEEK is preferred in view of its toughness and tensile strength combined with its low friction properties. In other variants of the invention, the washer could, for example have a composite construction and include both a low frictional polyemeric material, for example PEEK, and a suitable metal, which could for example be lined with the polymeric material.

It will be understood from the above that the term "low friction polymeric material" as used in this specification refers to a material which will generate reduced frictional resistance to screw rotation than would be the case in the absence of such material.

The illustrated embodiment includes a dental component in the form of an abutment and, in the final assembly, a crown or prosthetic tooth which is fixed to the abutment. It will however be understood that the dental component could be a coping or tooth prosthesis itself.

Many other modifications to the illustrated embodiment are also within the scope of the invention. Purely by way of example, the hexagonal section boss 16 could be replaced by an external boss with a different cross-sectional shape or by an internally engagable socket and the hexagonal section socket 34 could be replaced by a socket or other formation with a different cross-sectional shape, for example a square section socket, a torx socket or simply a slot.

The invention claimed is:

1. A dental implant assembly comprising:
an implant component configured to be engaged with a bone structure, the implant component having an internally threaded socket;
a dental component configured to be seated on the implant component, the dental component having a passage therethrough, the passage forming an inner ledge;
a screw having a head and a shank, the shank being configured to pass through the passage and to be screwed into the threaded socket of the implant component in order to clamp the dental component to the implant component responsive to the screw being torqued; and
a washer located on the shank of the screw between the head thereof and the inner ledge to aid in reducing friction between the head of the screw and the inner ledge of the passage of the dental component when the screw is torqued, the washer having an upper surface configured to engage the head of the screw and a lower surface configured to engage the inner ledge, the upper surface and the lower surface of the washer remaining substantially flat after the torqueing of the screw, the washer being made of or including PEEK (polyetheretherketone) and being held axially captive on the shank of the screw in an annular groove in the shank of the screw adjacent the head of the screw, and the washer being elastically stretchable and having a relaxed internal diameter that is (i) smaller than a maximum outer diameter of the shank of the screw and (ii) greater than an outer diameter of the annular groove such that the washer is readily rotatable in the annular groove.

2. The dental implant assembly according to claim 1 wherein the screw and washer form a preassembled unit before the screw is passed through the passage in the base of the dental component.

3. The dental implant assembly according to claim 1 wherein the groove is defined between the head and a radially enlarged region of the shank.

4. The dental implant assembly according to claim 1 wherein the elastic stretchability of the washer is sufficient to enable it to pass over the shank of the screw, from a distal end thereof, to be located in the groove.

5. The dental implant assembly according to claim 1 wherein the screw is made of stainless steel.

6. The dental implant assembly according to claim 5 wherein at least certain surfaces of the screw are coated or plated with a low friction material.

7. The dental implant assembly according to claim 6 wherein the screw includes threads plated with gold or a gold alloy.

8. The dental implant assembly according to claim 1 wherein the shank further includes a radially enlarged region positioned beneath the annular groove and above a main portion of the shank.

9. The dental implant assembly of claim 1, wherein a cross-sectional shape of the washer is generally rectangular after the torqueing of the screw.

10. A dental sub-assembly comprising:
a screw having a head and a threaded shank, the threaded shank being configured to pass through a passage in a base of a dental component to be screwed into a threaded socket in an implant component on which the dental component is seated in order to clamp the dental component to the implant component when the screw is tightened up; and
a washer located on the shank of the screw adjacent the head thereof in order to reduce friction between the head of the screw and the dental component when the screw is tightened up, the washer having an upper surface configured to engage the head of the screw and a lower surface configured to engage the base of the dental component, the upper surface and the lower surface of the washer remaining substantially flat after the tightening up of the screw, the washer being made of or including PEEK (polyetheretherketone) and being held axially captive on the shank of the screw in an annular groove in the shank of the screw adjacent the head of the screw, and the washer being elastically stretchable and having a relaxed internal diameter smaller than that of the shank of the screw but greater than that of a base of the annular groove so as to be rotatable in the groove.

11. The dental sub-assembly according to claim 10 wherein the groove is defined between the head and a radially enlarged region of the shank.

12. The dental sub-assembly according to claim 10 wherein the elastic stretchability of the washer is sufficient to enable it pass over the shank of the screw, from a distal end thereof, to be located in the groove.

13. The dental sub-assembly according to claim 10 wherein the screw is made of stainless steel.

14. The dental sub-assembly according to claim 13 wherein at least certain surfaces of the screw are coated or plated with a low friction material.

15. The dental sub-assembly according to claim 14 wherein the threads of the stainless steel are plated with gold or a gold alloy.

16. The dental implant assembly according to claim 8 wherein the relaxed internal diameter of the washer is less than a maximum outer diameter of the radially enlarged region of the shank.

17. The dental sub-assembly according to claim 10 wherein the shank further includes a radially enlarged region positioned beneath the base of the annular groove and above a main portion of the shank.

18. The dental sub-assembly according to claim 17 wherein the relaxed internal diameter of the washer is less than a maximum outer diameter of the radially enlarged region of the shank.

19. The dental sub-assembly of claim 10, wherein a cross-sectional shape of the washer is generally rectangular after the tightening up of the screw.

20. A dental implant assembly comprising:
an implant component having an internally threaded socket;
an abutment having a passage therethrough forming an inner ledge;
a screw having a head and a shank configured to pass through the passage of the abutment and to be screwed into the threaded socket of the implant component in order to clamp the abutment to the implant component responsive to the screw being torqued; and
a friction-reducing polymeric washer located on the shank of the screw between the head thereof and the inner ledge, the friction-reducing polymeric washer aiding in reducing friction between the head of the screw and the inner ledge of the passage of the abutment when the screw is torqued, the friction-reducing polymeric washer having an upper surface engaging the head of the screw and a lower surface engaging the inner ledge, the upper surface and the lower surface of the friction-reducing polymeric washer remaining substantially flat after the screw has received torque and the abutment is fixedly attached to the implant component.

21. The dental implant assembly of claim 20, wherein a cross-sectional shape of the friction-reducing polymeric washer is generally rectangular after the torqueing of the screw.

22. The dental implant assembly of claim 20, wherein the friction-reducing polymeric washer is made of or includes PEEK (polyetheretherketone).

23. The dental implant assembly of claim 20, wherein the friction-reducing polymeric washer is held axially captive on the shank of the screw in an annular groove in the shank of the screw adjacent the head of the screw.

24. The dental implant assembly of claim 23, wherein the friction-reducing polymeric washer is elastically stretchable and has a relaxed internal diameter that is (i) smaller than a maximum outer diameter of the shank of the screw and (ii) greater than an outer diameter of the annular groove such that the friction-reducing polymeric washer is readily rotatable in the annular groove.

25. The dental implant assembly of claim 20, wherein a cross-sectional shape of the friction-reducing polymeric washer is generally rectangular after the torqueing of the screw.

* * * * *